United States Patent [19]

Houtchens et al.

[11] Patent Number: 4,675,292

[45] Date of Patent: Jun. 23, 1987

[54] STABILIZATION OF GLUCOSE ISOMERASE

[75] Inventors: Robert A. Houtchens; Roberta C. Cheng; Karen M. McCoy; Carol C. Epstein, all of Midland; Norman G. Moll, Sanford, all of Mich.

[73] Assignee: The Dow Chemical Company, Midland, Mich.

[21] Appl. No.: 707,774

[22] Filed: Mar. 4, 1985

[51] Int. Cl.$^4$ .......................... C12P 19/24; C12N 9/96
[52] U.S. Cl. ........................................ 435/94; 435/188
[58] Field of Search .......................... 435/188, 94, 234

[56] References Cited

U.S. PATENT DOCUMENTS

| | | | |
|---|---|---|---|
| 3,915,797 | 10/1975 | Ishimatsu et al. | 435/94 |
| 3,982,997 | 9/1976 | Eaton et al. | 435/94 |
| 4,077,842 | 3/1978 | Cory | 435/188 |
| 4,144,127 | 3/1979 | Enokizono et al. | 435/176 |
| 4,308,349 | 12/1981 | Foley et al. | 435/94 |
| 4,411,996 | 10/1983 | Lloyd | 435/94 |
| 4,572,897 | 2/1986 | Amotz et al. | 435/177 |

*Primary Examiner*—Lionel M. Shapiro

[57] ABSTRACT

Extracellular enzymes are stabilized with a carboxyalkylated or phosphonoalkylated polymer having a molecular weight of at least 500 Daltons. Exemplified is the stabilization of the enzyme glucose isomerase used in a process to convert D-glucose to D-fructose. In a preferred embodiment of the invention the feedstream containing the substrate is contacted initially with the stabilizer and then with the enzyme. In this system the stabilizer and enzyme are maintained in separate reactors. This separation, advantageously, results in a higher half-life for the enzyme.

20 Claims, 1 Drawing Figure

STABILIZATION OF GLUCOSE ISOMERASE

BACKGROUND OF THE INVENTION

Microbe-catalyzed processes are particularly useful in the production of a variety of chemicals known as fine or specialty chemicals.

Perhaps the most important commercial use of microbe-catalyzed processes is in the food industry. Exemplary of such processes is the production of high fructose corn syrup (HFCS) catalyzed by immobilized glucose isomerase. This process converts glucose to an approximately equimolar mixture of fructose and glucose; this mixture is referred to as HFCS.

Examples of other chemicals prepared by microbe-catalyzed processes are the L-amino acids, which are useful as food additives, in animal feed, and in medicinals. Though chemical synthesis may be simpler than fermentations at times to prepare amino acids, the chemical process almost always yields a racemic mixture of amino acids. This racemic mixture then has to be resolved to give the biologically-active L-amino acid. On the other hand, a microbe-catalyzed process will yield the L-amino acid predominantly.

Immobilization of an enzyme which catalyzes a microbe-catalyzed process generally gives better yields of desired product and preserves enzyme integrity. With regard to extracellular enzymes, immobilization is the physical or chemical containment of the enzyme so that the enzyme can conveniently be separated from the product and reused. Stabilization of enzymes by chemical stabilizers also preserves enzyme integrity. The immobilization or stabilization of the enzyme can be done while the enzyme is still in the living microbe (intracellular), or when the enzyme is in the cell-free state. The immobilization or stabilization techniques will vary in accord with these two enzyme states. Thus, it should be appreciated that immobilization or stabilization conditions effective for intracellular enzymes will not necessarily be appropriate for extracellular enzymes, and vice versa.

Prior art relating to the immobilization or stabilization of extracellular enzymes can be exemplified by the following U.S. patents:

U.S. Pat. No. 3,915,797—Enzyme bonded to a substantially water-insoluble anion exchange resin.

U.S. Pat. No. 3,982,997—Glucose isomerase adsorbed to the internal surfaces of a high surface area porous inorganic support material.

U.S. Pat. No. 4,077,842—A stabilized glucose isomerase concentrate is prepared by contacting an aqueous mixture containing cell-free glucose isomerase and a water-miscible organic solvent with a substantially water soluble magnesium salt.

U.S. Pat. No. 4,144,127—Glucose isomerase is immobilized by adsorption onto a colloidal silica.

U.S. Pat. No. 4,411,996—Glucose isomerase is stabilized by intramolecular crosslinking and copolymerization into a polymer matrix.

BRIEF SUMMARY OF THE INVENTION

Stabilization of extracellular enzymes is realized by contacting the feed stream or enzymes with a carboxyalkylated or phosphonoalkylated polymer having a molecular weight of at least 500 Daltons. Specifically exemplified herein is the use of a carboxymethylated polyamine and glucose isomerase to convert D-glucose to D-fructose. The relatively high molecular weight of the polymer allows for separation of the polymer-stabilizer from the glucose substrate solution. This eliminates the need for removal of the polymer stabilizing agent from the substrate with, for example, ion exchange resins. Tests have shown that glucose isomerase half-life in the presence of carboxymethylated Purifloc C-31 (Trademark of The Dow Chemical Company for a polyamine polymer prepared by reacting ethylenedichloride with a mixture of ethyleneimine oligomers) is 760 hours, whereas in the absence of the polymer, the glucose isomerase half-life is 12.7 hours. This clear difference in the enzyme half-life vividly illustrates the utility of the subject invention and products obtained thereby.

The polymeric chemical stabilizer of the invention can be retained within a reactor with the extracellular enzyme, or preferably, retained in a reactor upstream from the enzyme. Separation of the enzyme and stabilizer results in a significantly higher half-life for the enzyme.

Further stabilization of the immobilized enzyme is realized after encapsulating the immobilized enzyme with protective layers of polymer(s). This added stabilization of enzyme is particularly advantageous for processes carried out at lower pH's, e.g., pH 6-8.5.

REFERENCE TO THE DRAWING

The drawing depicts a schematic of the preferred invention process to convert D-glucose to D-fructose.

DETAILED DESCRIPTION OF THE INVENTION

Figure 1:
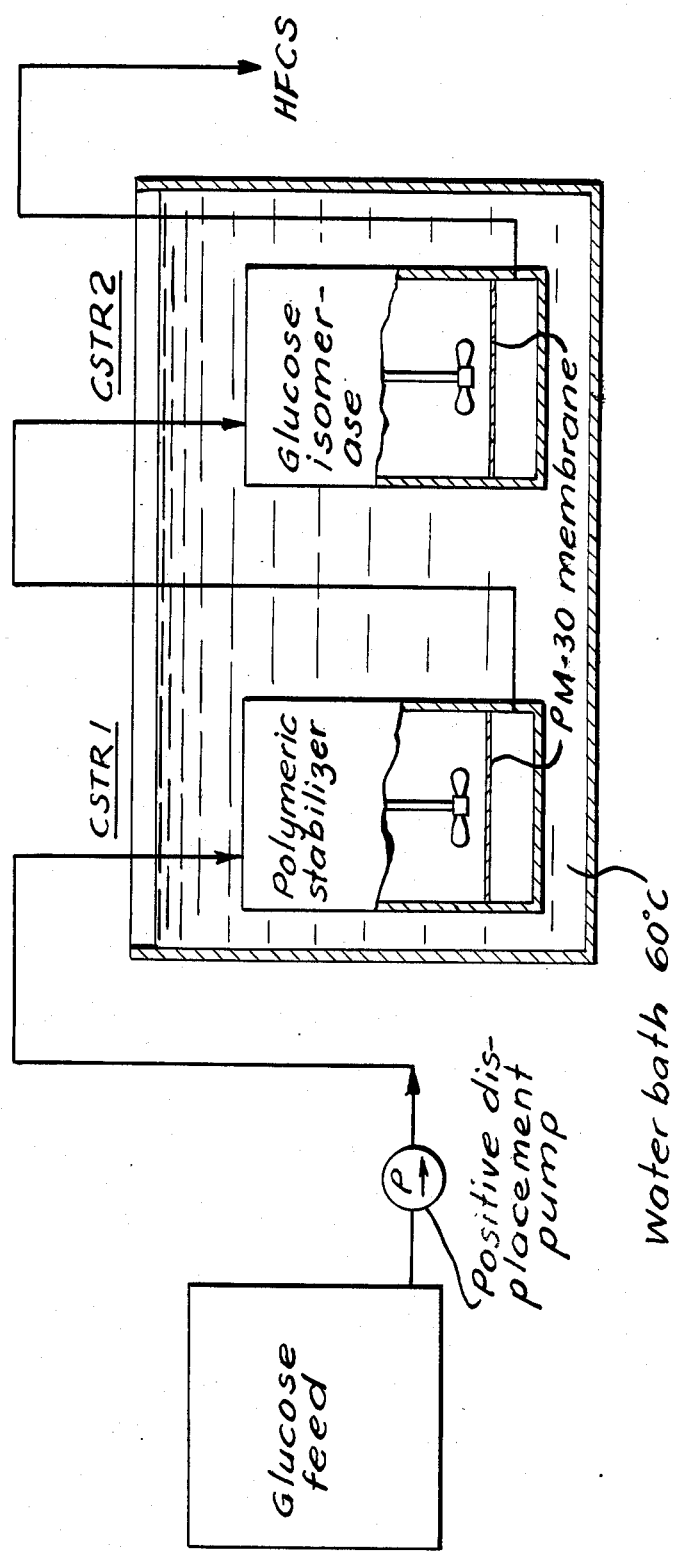

The subject invention concerns a process to stabilize extracellular (cell free) enzymes. It is specifically exemplified herein by the well-known enzyme glucose isomerase. Similar techniques can be used with other enzymes. Necessary modifications to accommodate the use of such other enzymes are well within the skill of those in the microbiological enzyme art. Thus, the subject disclosure provides a sufficient disclosure to use the invention process with any extracellular enzymes.

With regard to glucose isomerase, this enzyme can be produced by a large number of microbes as disclosed in U.S. Pat. No. 4,308,349, Col. 1, lines 26-32. The Ampullariella species of this patent have been found to be especially good producers of glucose isomerase. Hence, examples depicting the invention process, disclosed hereinafter, disclose the use of this glucose isomerase-producing microbe. However, it should be understood that this illustrative use is by no means a limitation as to the source of glucose isomerase. The many other glucose isomerase-producing microbes known to the art and available to the public also can be used to produce the glucose isomerase.

The extracellular enzyme, preferably, is separated from the polymeric chemical stabilizer of the invention. The polymeric chemical stabilizer of the invention is a carboxyalkylated or phosphonoalkylated polymer having a molecular weight of at least 500 Daltons. Carboxyalkylating is well known in the art. See U.S. Pat. No. 3,424,790, which discloses a process for preparing carboxymethylated polyethyleneimine (CM-PEI). The polymer also can be modified by phosphonoalkylation. Phosphonoalkylation is a well-known art process. See Westerback et al. J. Am. Chem. Soc. 87, 2567 (1965). The alkyl in the above is $-(CH_2)_n-$ wherein $n=1-3$ (preferably n=1), or —(CHR)—(CH$_2$)$_n$— wherein R=methyl, ethyl, propyl, or isopropyl, and n=1 or 2.

The polyelectrolyte can be either fully or partially carboxymethylated. The amount of modification of the polyelectrolyte, e.g., carboxymethylation of the polyethyleneimine, can be varied from about 0.1 to about 2.0 equivalents of polyelectrolyte. This is accomplished by reacting various amounts of chloroacetic acid (from 0.1 to 2.0 equivalents of the total nitrogen content in PEI) with the polyelectrolyte. The extent of carboxymethylation is proportional to the ratio of chloroacetic acid to total nitrogen of polyelectrolyte.

Polymers within the scope of the subject invention, which can be modified as disclosed above, are classified as cationic polyelectrolytes, for example, polyamines (primary, secondary, and tertiary amines); polyaminoacids, for example, polylysine; cationic polyacrylamides, for example, polydimethylaminopropylmethacrylamide; cationic poly(vinyl chloride), for example, poly(vinyl chloride) aminated with triethylene tetraamine; cationic copolymers, for example, styrene-dimethylaminopropylmethacrylamide (50:50) copolymer; and cationic flocculants, for example, Purifloc C-31. Examples of carboxymethylated polymeric materials which have demonstrated glucose isomerase stabilization employing the procedures described herein are shown in Table I.

Encapsulation of the immobilized enzyme greatly enhances the stability of the enzyme. Polymers which can be used to encapsulate the enzyme are the same as described herein for stabilizing the enzyme.

Following are examples that illustrate the process and products of the invention. These examples should not be construed as limiting. All percentages are by weight and all solvent mixture proportions are by volume unless otherwise noted.

EXAMPLE 1

Preparation of Enzyme

Soluble glucose isomerase can be prepared as disclosed in the examples of U.S. Pat. No. 4,308,349. Glucose isomerase produced by different microorganisms, as disclosed in U.S. Pat. No. 4,411,996, Col. 4, lines 20-52, also can be used in the subject invention. The enzyme can be used in any state of purity ranging from a crude disruptate to >95% of the protein as glucose isomerase.

EXAMPLE 2

Isomerization of D-Glucose to D-Fructose

In a preferred process for using the polymeric chemical stabilizers of the invention to convert D-glucose to D-fructose, the stabilizer is retained within a continuous stirred-tank reactor, upstream from the enzyme, by the use of an ultrafiltration membrane at the exit of the reactor. The membrane must have a pore size small enough to retain the polymeric stabilizer. The substrate feedstream, e.g., glucose, is passed through the reactor containing the polymeric stabilizer of the invention. The stabilizer is retained in the reactor by the membrane, and the feedstream is forced across the membrane by the pressure gradient. An Amicon Diaflo PM-30 (Trademark of Amicon, Danvers, Mass.) membrane, and the like, can be used in this process to convert glucose to fructose. The feedstream then passes through the second reactor containing the enzyme, e.g., glucose isomerase. Advantageously, the enzyme can be encapsulated, as described above. The enzyme converts a portion of the glucose to fructose and the glucose-fructose mixture passes through the secondary membrane, as described above.

The parameters of the process to convert D-glucose to D-fructose, described above, are as follows:

Reactor temperature: 50°–100° C.
Mean residence time: 0.05–6 hrs
Feedstream pressure: 0.1–100 psi
Glucose feed concentration: 10–60% w/w
Stabilizing polymer concentration: $4 \times 10^{-4}\%$–40% (w/v)
Mg++ concentration: 0.1–20 mM
Feedstream pH: 5.0–9.0
Polymer molecular weight: 500 Daltons or greater.

At lower reactor temperatures the enzyme does not catalyze the reaction and at higher temperatures the enzyme denatures. Residence time is a function of enzyme loading. For commercial applications, residence time should be long enough to isomerize at least 42% of the glucose to fructose; however, residence time should not be unnecessarily long to avoid sugar degradation. Minimum feedstream pressure is required to drive the ultrafiltration and is determined by the required residence time, the particular membrane, and the feedstream viscosity. Maximum pressure is determined by the pressure limits of the reactor. Glucose concentration in the feedstream should be as high as possible for economy of water and process volume; however, if viscosity or diffusivity limits reactor performance, lower concentrations may be used. Polymeric stabilizer, concentration should be minimized for reasons of economy, but must be present at levels that stabilize the enzyme. Magnesium ion is typically necessary for feasible enzyme activity but should be minimized for economy. Suitable salts can be used, for example, magnesium sulfate, magnesium phosphate, and the like. The pH must be within limits for enzyme activity and stability. Polymeric stabilizer molecular weight must be great enough to facilitate its immobilization and separation from the product.

Polymeric chemical stabilizer or glucose isomerase can be immobilized by entrapment within an ultrafiltration device, microporous support or capsule. The stabilizer can be covalently attached to a support such as a resin bead or membrane. Glucose isomerase can be bonded through ionic interaction to ion exchange materials such as ion exchange resin beads, membranes, chelating resins or metal containing supports such as silica or alumina. All of these procedures are well known in the art.

Also, the stabilizing polymer can be converted to a resin by crosslinking the polymer to form an insoluble bead by procedures well known in the art. Insoluble extracellular enzyme particles and polymeric stabilizer particles can be mixed together and used in a reactor column.

As stated above, separation of the polymeric chemical stabilizer from the enzyme is the preferred process for use of the stabilizer to enhance the half-life of the enzyme, and, thus, yield a more efficient enzymatic conversion process.

EXAMPLE 3

Immobilization of Glucose Isomerase on Macroporous Weak Anion Exchange Resin The ion exchange resin, Dowex MWA-1 (Trademark of The Dow Chemical Company for a macroporous weak base anion exchange resin) (200 gm, wet) was washed with 1 liter of methanol, 200 ml of water, 100 ml of 1.0N hydrochloric acid and again with 1 liter of water. The washed resin was allowed to equilibrate in 1 liter of sodium phosphate buffer (0.1M, pH 7.0) at 60° C. and 150 rpm in a shaker bath for 24 hr. The procedure was repeated 2 more times with fresh buffer. At the end, the pH of the wash was about 6.9. The resin was then collected on a sintered glass funnel (coarse), and washed with 500 ml of the same buffer and dried by suction.

To immobilize the enzyme, 130 gm of the washed resin was weighed into 1500 ml of a partially purified glucose isomerase solution extracted from the Ampullariella 3876 organism which had 11 GIU/ml of activity (1 GIU is defined as the GI activity which catalyzes the isomerization of 1 micromole of glucose to fructose per minute under standard assay conditions). The slurry in a 2.8 l Fernbach flask was incubated at 60° C. and 150 rpm for 30 hr. Upon termination, the supernatant was assayed for GI activity as a check of the completeness of the immobilization, which was found to be 0.04 GIU/ml, or 4% of the initial activity. The MWA-1 immobilized GI was collected on the funnel, and washed with 1 liter of water and suction dried. The activity of the immobilized enzyme was found to be 104 GIU/gm-wet (48.5% solid).

Stability Test with Polymeric Stabilizer

The immobilized glucose isomerase (4 gm wet) was packed into a column reactor (0.9×25 cm) and stability of the immobilized enzyme was tested with the substrate solution pretreated according to the following procedure. The glucose solution (50% w/v, containing 3 mM Mg++ and 0.02% sodium azide) was first passed through a polymeric stabilizer which was retained in a 200 ml continuous stirred-tank reactor (Amicon stirred cell, model #8200 [Trademark of Amicon]) by the use of an ultrafiltration membrane (Amicon Diaflo PM-30 [Trademark of Amicon]) at the exit of the reactor. The stabilizer used in this experiment was CM-PEI, using 3.5 milliequivalents of PEI for the entire experiment to pretreat 60 l of glucose solution (at about 30 ml/hr for 2000 hr).

The stability of the MWA-1 immobilized GI tested at 60° C. with pretreated glucose was compared to that with the untreated glucose feed, and results (half-life times) under various conditions are shown in Table II.

EXAMPLE 4

The immobilized glucose isomerase used and also the test conditions were identical to those in Example 3, except that a fresh sample of CM-PEI (equivalent to 3.5 millimoles of PEI) was added and the used CM-PEI was discarded every 350 hr during the test period. Thus for a 2000 hr experiment, six changes of CM-PEI were made. Half-life time is shown in Table II.

TABLE I

Polymeric Chemical Stabilizers of Glucose Isomerase

| | t ½ (hrs) at pH 7.0 and 60° C. |
|---|---|
| CM-PEI-600* | 1230 |
| CM-Purifloc C-31** | 760 |
| CM-PEOX*** (100% hydrolyzed) | 1695 |
| CM-PEOX (85% hydrolyzed) | 1032 |

*PEI-600 is a polyethyleneimine product sold by Cordova Chemical Company, Muskegon, MI.
**Purifloc C-31 is a trademark of The Dow Chemical Company, Midland, MI from which the product can be purchased. The product is a polyamine polymer prepared by reacting ethylenedichloride with a mixture of ethyleneimine oligomers.
***PEOX is polyethyloxazoline-hydrolysis of polyethyloxazoline yields a linear polyethyleneamine.

TABLE II

Half-Life Time of MWA-1 Immobilized Glucose Isomerase with Pretreated Glucose at 60° C.

| # | Pretreatment | pH | First t ½, hrs |
|---|---|---|---|
| 1 | None (control) | 7.4 | 450 |
| 2 | CM-PEI (one charge) | 7.4 | 1300 |
| 3 | CM-PEI (change every 350 hr) | 7.4 | 1350 |
| 4 | None (control) | 8.2 | 475 |
| 5 | CM-PEI (one charge) | 8.2 | 1000 |
| 6 | CM-PEI (change every 350 hr) | 8.2 | 1200 |

We claim:

1. A process for stabilizing extracellular glucose isomerase used to convert D-glucose in a feedstream to D-fructose which comprises contacting said feedstream or said extracellular glucose isomerase with a carboxyalkylated or phosphonoalkylated cationic polyelectrolyte having a molecular weight of at least 500 Daltons.

2. The process of claim 1 wherein said cationic polyelectrolyte is a carboxymethylated cationic polyelectrolyte.

3. The process of claim 1 wherein said glucose isomerase is produced by glucose isomerase-producing microbial cells belonging to the genus Ampullariella.

4. The process of claim 3 wherein said Ampullariella glucose isomerase-producing cells are Ampullariella species 3876, ATCC 31351.

5. The process of claim 1 wherein the alkyl of the carboxyalkylated or phosphonoalkylated moiety of said carboxyalkylated or phosphonoalkylated cationic polyelectrolyte is —$(CH_2)_n$— wherein n=1-3, or —(CHR)—$(CH_2)_n$— wherein R=methyl, ethyl, propyl, or isopropyl, and n=1 or 2.

6. The process of claim 1 wherein said extracellular glucose isomerase is immobilized.

7. The process of claim 1 wherein said extracellular glucose isomerase is encapsulated.

8. The process of claim 7 wherein the glucose isomerase is encapsulated with a carboxyalkylated or phosphonoalkylated cationic polyelectrolyte.

9. The process of claim 8 wherein the alkyl of the carboxyalkylated or phosphonoalkylated moiety of said carboxyalkylated or phosphonoalkylated cationic polyelectrolyte is —$(CH_2)_n$— wherein n=1-3, or —(CHR)—$(CH_2)_n$— wherein R=methyl, ethyl, propyl, or isopropyl, and n=1 or 2.

10. Stabilized extracellular glucose isomerase comprising extracellular glucose isomerase and a carboxyalkylated or phosphonoalkylated cationic polyelectrolyte having a molecular weight of at least 500 Daltons, in the presence of a glucose substrate.

11. Stabilized extracellular glucose isomerase, according to claim 10, wherein the alkyl of the carboxyalkylated or phosphonoalkylated moiety of said carboxyalkylated or phosphonoalkylated cationic polyelectrolyte is $-(CH_2)_n-$ wherein n=1-3, or $-(CHR)-(CH_2)_n-$ wherein R=methyl, ethyl, propyl, or isopropyl, and n=1 or 2.

12. Stabilized extracellular glucose isomerase, according to claim 10, wherein said cationic polyelectrolyte is a carboxymethylated cationic polyelectrolyte.

13. Stabilized extracellular glucose isomerase, according to claim 10, wherein the glucose isomerase is immobilized.

14. Stabilized extracellular glucose isomerase, according to claim 10, wherein the glucose isomerase is encapsulated.

15. Stabilized extracellular glucose isomerase, according to claim 14, wherein the glucose isomerase is encapsulated with a carboxyalkylated or phosphonoalkylated cationic polyelectrolyte.

16. Stabilized extracellular glucose isomerase, according to claim 15, wherein the alkyl of the carboxyalkylated or phosphonoalkylated moiety of said carboxyalkylated or phosphonoalkylated cationic polyelectrolyte is $-(CH_2)_n-$ wherein n=1-3, or $-(CHR)-(CH_2)_n-$ wherein R=methyl, ethyl, propyl, or isopropyl, and n=1 or 2.

17. A process for preparing D-fructose from D-glucose which comprises initially contacting a feedstream containing D-glucose with a stabilizer comprising a carboxyalkylated or phosphonoalkylated cationic polyelectrolyte having a molecular weight of at least 500 Daltons, and then contacting said feedstream with glucose isomerase.

18. The process of claim 17 wherein said glucose isomerase is immobilized.

19. The process of claim 17 wherein said glucose isomerase is encapsulated.

20. The process of claim 17 wherein the alkyl of the carboxyalkylated or phosphonoalkylated moiety of said carboxyalkylated or phosphonoalkylated cationic polyelectrolyte is $-(CH_2)_n-$ wherein n=1-3, or $-(CHR)-(CH_2)_n-$ wherein R=methyl, ethyl, propyl, or isopropyl, and n=1 or 2.

* * * * *